United States Patent [19]

Durda et al.

[11] Patent Number: 5,672,471
[45] Date of Patent: Sep. 30, 1997

[54] ASSAY FOR DETECTION AND/OR QUANTIFYING A MAMMALIAN IGA ANTIBODY RESPONSE TO EPSTEIN-BARR VIRUS MEMBRANE ANTIGEN USING EBV-MA GP 350/220 LACKING THE TRANSMEMBRANE ANCHOR DOMAIN

[75] Inventors: Paul John Durda, Needham; Elliott Dan Kieff, Brookline, both of Mass.; Gary Richard Pearson, Great Falls, Va.; Harvey Rabin, North Andover; Marcia Delaney Sullivan, Methuen, both of Mass.

[73] Assignee: E. I. Du Pont de Nemours and Company, Wilmington, Del.

[21] Appl. No.: 542,234

[22] Filed: Oct. 12, 1995

Related U.S. Application Data

[63] Continuation of Ser. No. 291,321, Aug. 16, 1994, abandoned, which is a continuation of Ser. No. 933,601, Aug. 20, 1992, abandoned, which is a continuation of Ser. No. 546,338, Jun. 29, 1990, abandoned.

[51] Int. Cl.⁶ ............... C12Q 1/70; G01N 33/563; G01N 33/543
[52] U.S. Cl. ............... 435/5; 436/513; 436/518; 436/812; 436/813
[58] Field of Search ............... 435/5; 436/513, 436/518, 812, 813

[56] References Cited

U.S. PATENT DOCUMENTS 4,707,358  11/1987  Kieff et al. ............... 435/5

FOREIGN PATENT DOCUMENTS

| | | |
|---|---|---|
| 0151179 | 8/1985 | European Pat. Off. . |
| 151059 | 8/1985 | European Pat. Off. . |
| 0173254 | 3/1986 | European Pat. Off. . |
| 0260012 | 3/1988 | European Pat. Off. . |
| 2573533 | 5/1986 | France . |
| WO90/04176 | 4/1990 | WIPO . |

OTHER PUBLICATIONS

Emini, E. A. et al., Antigenic Analysis of the Epstein–Barr Virus Major Membrane Antigen Expressed in Yeast and Mammalian Cells: Implications for the Development of a Subunit Vaccine, *Virology*, 166, pp. 387–393, 1988.
Uen et al., Int. J. Cancer, 41:479–482 (1988).
Hopkins et al., J. Infectious Diseases, 146(6):734–740 (Dec. 1982).
Whang et al., J. of Virology, 61(6):1796–1807 (Jun. 1987).
Zhu et al., Int. J. Cancer, 37:689–691 (1986).
Pi et al., J. Virological Methods, 15:33–39 (1987).
Luka et al., J. Immunological Methods, 67:145–156 (1984).
Pearson et al., Human Herpesvirus Infections, Lopez and Roizman (eds.), pp. 211–220 (1986).
James et al., Clin. Microbiol. Rev., 3:132–152 (Apr. 1990).
Hummel et al., J. Virol., 49:413–417 (1984).
Beisel et al., J. Virol., 54:665–674 (1987).
Qualtiere et al., Immunology, 79:616–620 (Jan. 1982).
Qualtiere et al., J. Immunology, 129(2):814–818 (Aug. 1982).
Yi et al., Intervirology, 13:162–168 (1980).
Henle et al., Int. J. Cancer, 17:1–7 (1976).
Zeng et al., AIDS Research, vol. 2, Supp. 1, pp. S7–S15 (1986).
Halprin et al., Annals of Internal Medicine, 104:331–337 (1986).

*Primary Examiner*—Marian C. Knode
*Assistant Examiner*—Donna C. Wortman

[57] ABSTRACT

This disclosure concerns an assay for detecting and/or quantifying a mammalian IgA antibody response to EBV-MA with an immobilized EBV-MA gp 350/220 lacking the transmembrane anchor domain.

18 Claims, 4 Drawing Sheets

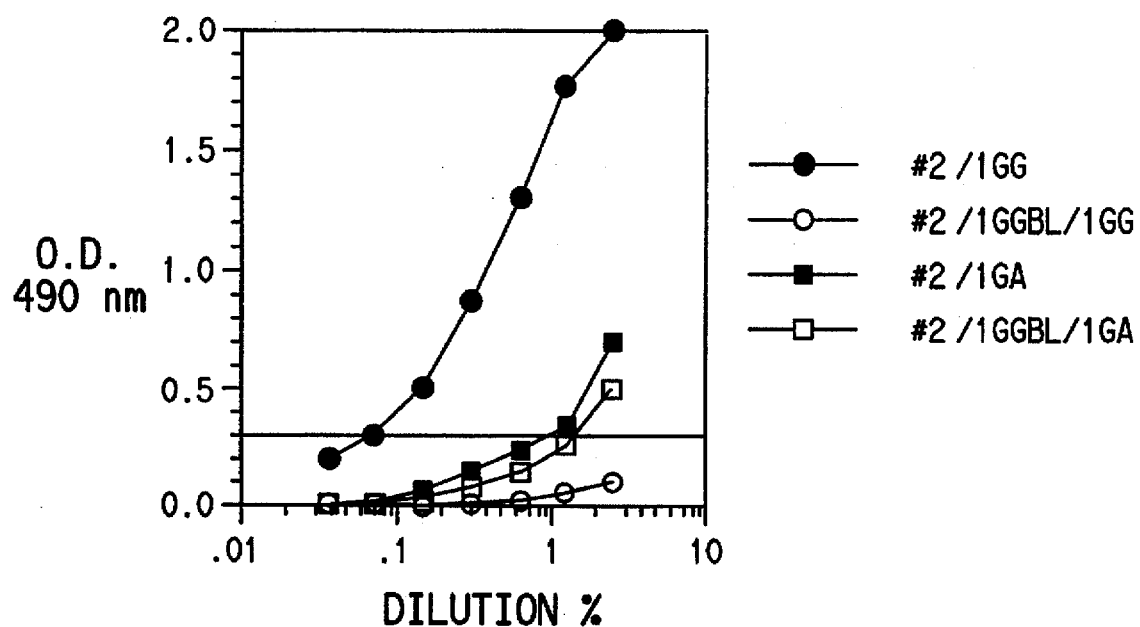
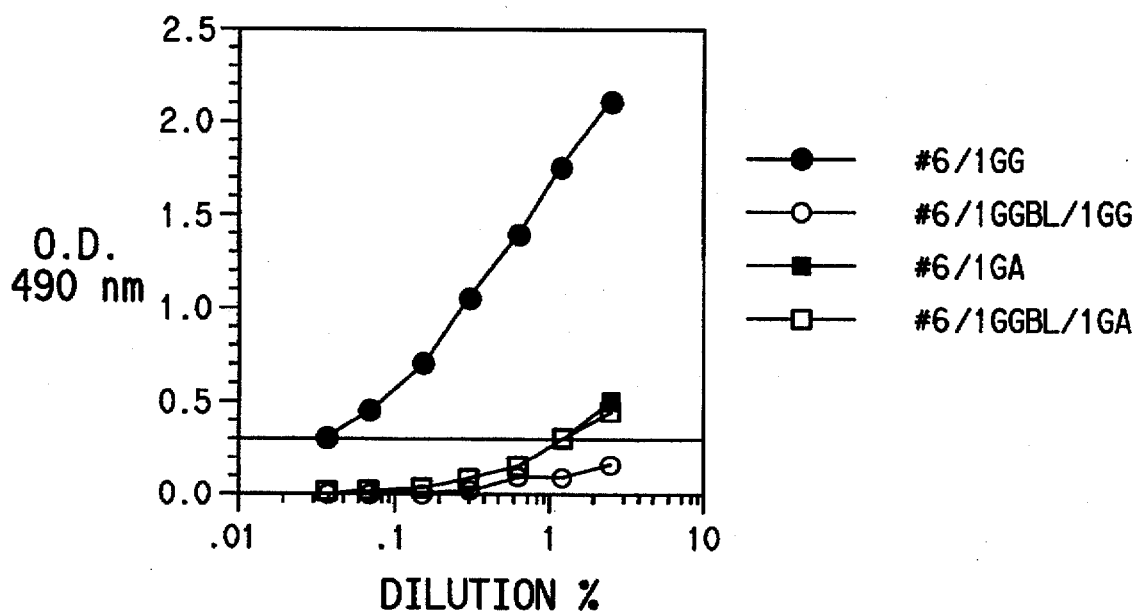

ASSAY FOR DETECTION AND/OR QUANTIFYING A MAMMALIAN IGA ANTIBODY RESPONSE TO EPSTEIN-BARR VIRUS MEMBRANE ANTIGEN USING EBV-MA GP 350/220 LACKING THE TRANSMEMBRANE ANCHOR DOMAIN

This is a continuation of application Ser. No. 08/291,321 filed Aug. 16, 1994, now abandoned which is a continuation of application Ser. No. 07/933,601 filed Aug. 20, 1992, now abandoned which is a continuation of application Ser. No. 07/546,338 filed Jun. 29, 1990, now abandoned.

FIELD OF THE INVENTION

This invention relates to diagnostic assays which detect and/or quantify mammalian antibody responses to Epstein-Barr virus (EBV) antigens and, in particular, to assays which detect and/or quantify human IgA antibody responses to EBV membrane antigen (MA).

BACKGROUND OF THE INVENTION

EBV, a human herpes virus, is ubiquitous in humans. Antibodies to polypeptides of the virus are present in over 80% of human serum samples from the United States and in even higher percentages from populations in Asia and Africa. Although it is prevalent throughout the world, the consequences of EBV infection vary among different populations. The virus is responsible for infectious mononucleosis in Western countries and is implicated in Burkitt's lymphoma in Africa and nasopharyngeal carcinoma (NPC) in Asia. NPC is a major form of cancer in southern China where incidence rates are as high as 100/100,000 annually.

The possibility that elevated IgA levels in NPC might be due to EBV-specific antibodies was reported by Henle et al. in Int. J. Cancer, 17:1–7 (1976). Specifically, an increase in titer of serum IgA antibodies to EBV viral capsid antigen (VCA) and EBV-induced early antigen (EA) in NPC patients using an indirect immunofluorescence assay (IFA) was described. This IFA has been a standard technique for detecting IgA antibodies to EBV antigens.

Zeng et al., AIDS Research, Vol. 2, Supplement 1, pages S7–S15 (1986), reported that EBV IgA early antigen (EA) and IgA MA antibodies are more specific for NPC than IgA VCA antibody. IgA and IgG antibodies to EBV MA were detected using IFA in sera from NPC patients. This group also reported on immunoenzymatic assays developed for detection of IgG and IgA antibodies to VCA which have been used extensively in China for screening the general population to identify individuals at risk for NPC.

Typically, the IFAs and enzyme-linked immunosorbent assays (ELISAs) which have been used to detect EBV antigens employ native antigen, either as whole EBV-infected fixed cells, virus infected cell lysates, or affinity purified antigens from virus infected cell lysates. Halprin et al., Annals of Internal Medicine, 104:331–337 (1986) described an ELISA of antibodies to measure titers of IgG antibodies against bacterially synthesized EBV nuclear and early antigens in patients with infectious mononucleosis and NPC.

Luka et al., J. Immunological Methods, 67: 145–156 (1984) describe an ELISA developed for the major EBV associated antigens which was based on purified protein components of VCA, EA, MA, and the nuclear antigen (EBNA). The antigens, except EBNA, were purified on immunoaffinity columns containing monoclonal antibodies.

Pearson et al., Human Herpesvirus Infections, Lopez and Roizman (eds.), pages 211–220 (1986), describe the value of monoclonal antibodies in the development of new diagnostic assays for EBV.

Uen et al., Int. J. Cancer, 41:479–482 (1988), describe a three-step ELISA for detecting IgA antibodies to purified EBV polypeptides. It was used to measure antibodies to the major VCA (gp125) and MA complexes (gp250/200).

U.S. Pat. No. 4,707,358, issued to Kieff et al. on Nov. 17, 1987 and European Patent Application Publication No. 151,079, published on Aug. 7, 1985 are directed to identification of the EBV DNA which encodes the protective immunogenic proteins gp350 and gp220.

James et al., Clin. Microbiol. Rev. 3:132–152 (April 1990), describe a number of several commercially available assays to detect total antibody, IgG or IgM antibodies to EBV antigens.

Hummel et al., J. Virol., 49:413–417 (1984), report that the genes encoding the two major EBV membrane glycoproteins (gp350/300 and gp220/200) have been mapped to a 5-kilobase fragment of the viral genome (BamHI-L). Beisel et al., J. Virol. 54:665–674 (1987), determined that the two major outer envelope glycoproteins are encoded by the same gene. Whang et al., J. Virol., 61(6):1796–1807 (June 1987), describe the expression of the EBV gp350/220 gene in rodent and primate cells. It is stated that rat pituitary cells (GH3 cell line) were transfected with the gp350/220 gene and a clone was established (GH3Δ19) which secreted high amounts of a truncated form of gp350/220 (lacking the transmembrane anchor domain) into culture supernatant.

SUMMARY OF THE INVENTION

This invention concerns an assay for detecting and/or quantifying a mammalian antibody response to EBV-MA which comprises:

a) incubating a sample suspected to contain EBV-MA antibodies with immobilized EBV-MA; and b) detecting and/or quantifying the product of step (a) by reacting the product of step (a) with a detector reagent which is capable of binding mammalian antibodies specific for EBV-MA.

BRIEF DESCRIPTION OF THE DRAWINGS

FIG. 2 shows a blocking experiment on samples found to be negative by IFA and found to be low positive having a titer of 1:40 using the assay of this invention.

FIG. 3 shows a blocking experiment on samples found to be negative by IFA and found to be low positive having a titer of 1:40 using the assay of this invention.

DETAILED DESCRIPTION OF THE INVENTION

Figure 1:
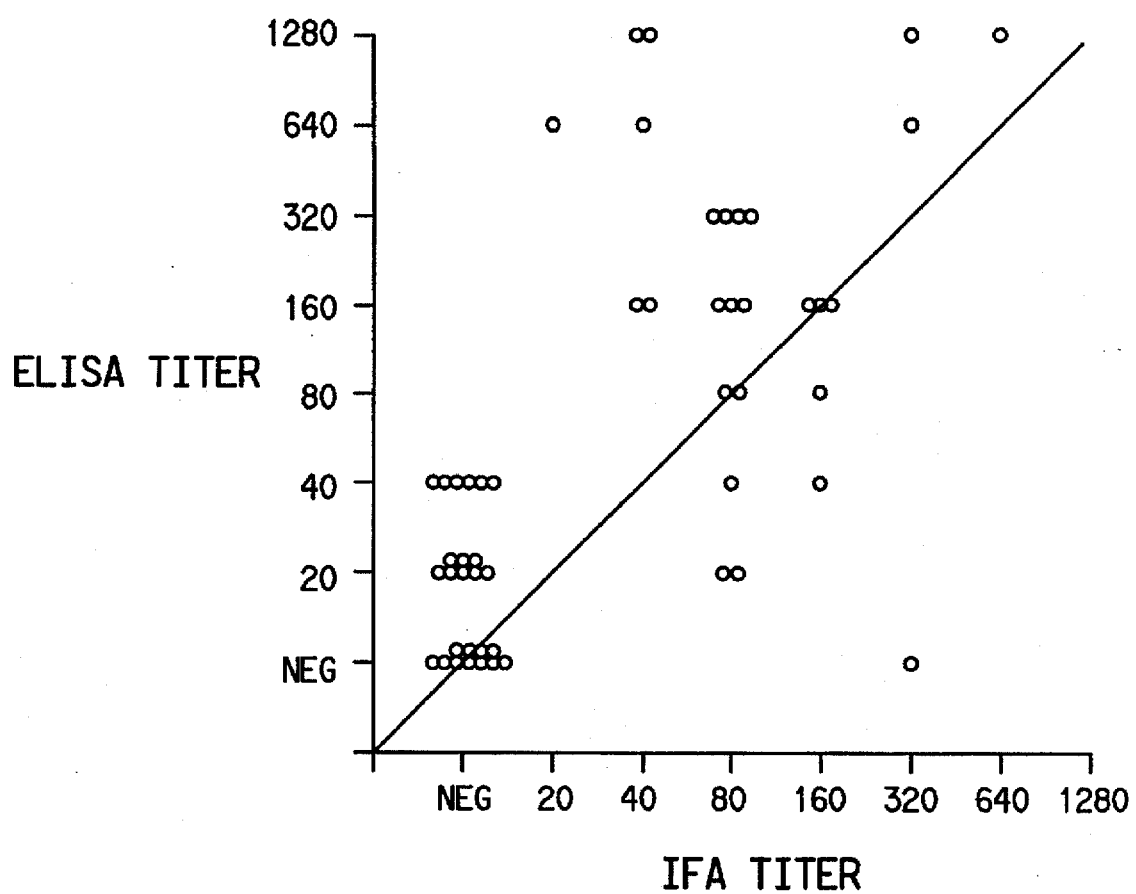
FIG. 1 is a graph depicting a comparison of ELISA vs. IFA of anti-EBV-MA titers in patient sera.
Figure 4:
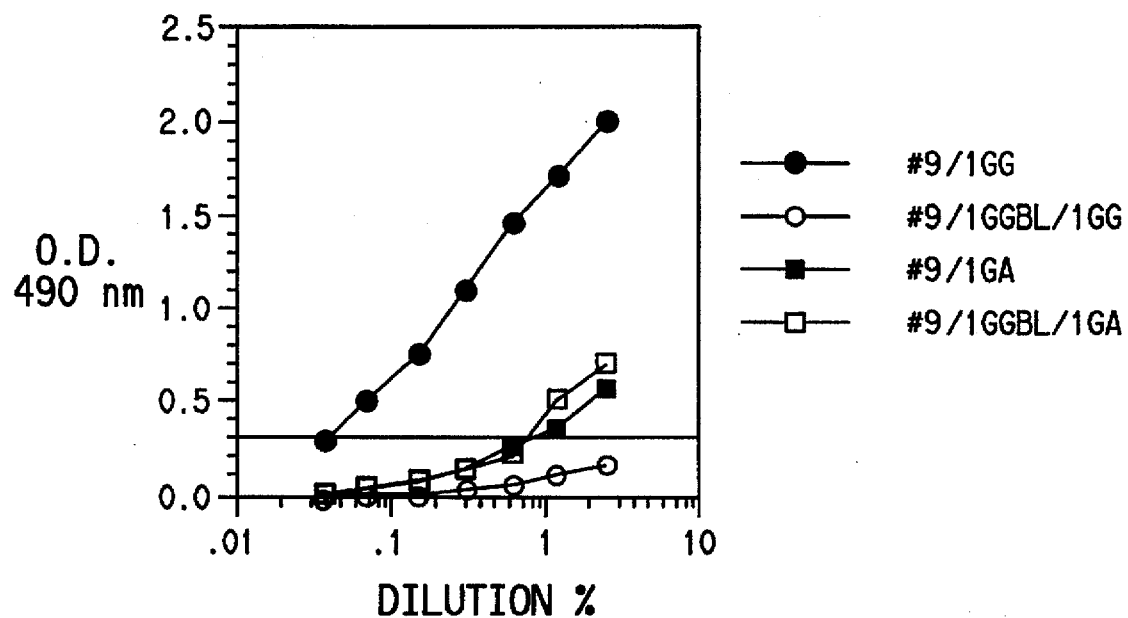
FIG. 4 shows a blocking experiment on samples found to be negative by IFA and found to be low positive having a titer of 1:40 using the assay of this invention.
Figure 5:
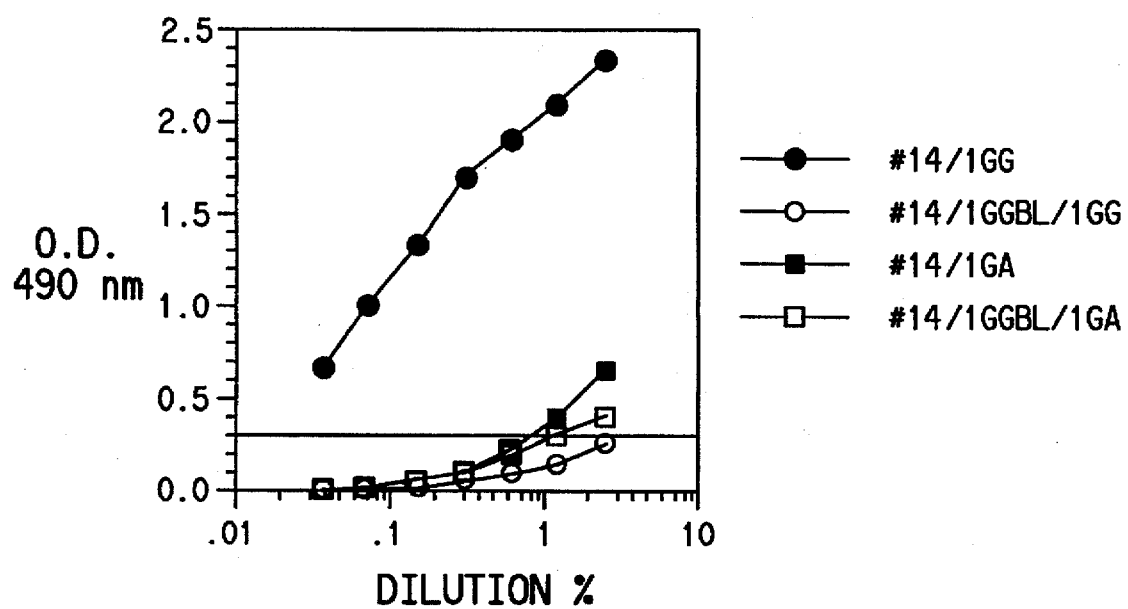
FIG. 5 shows a blocking experiment on samples found to be negative by IFA and found to be low positive having a titer of 1:40 using the assay of this invention.
Figure 6:
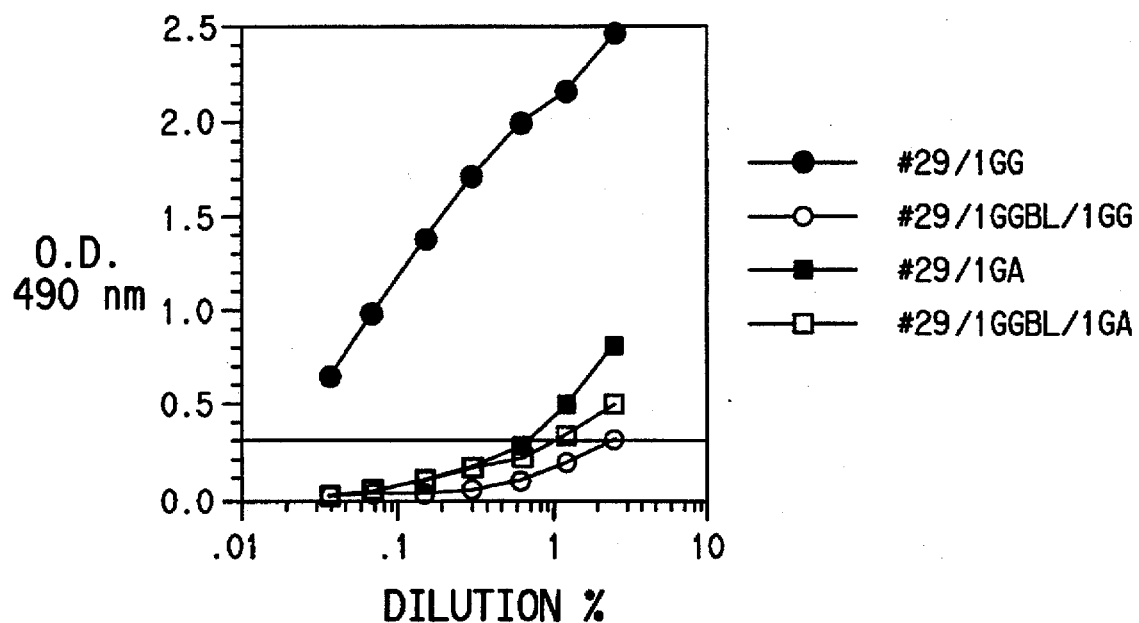
FIG. 6 shows a blocking experiment on samples found to be negative by IFA and found to be low positive having a titer of 1:40 using the assay of this invention.
Figure 7:
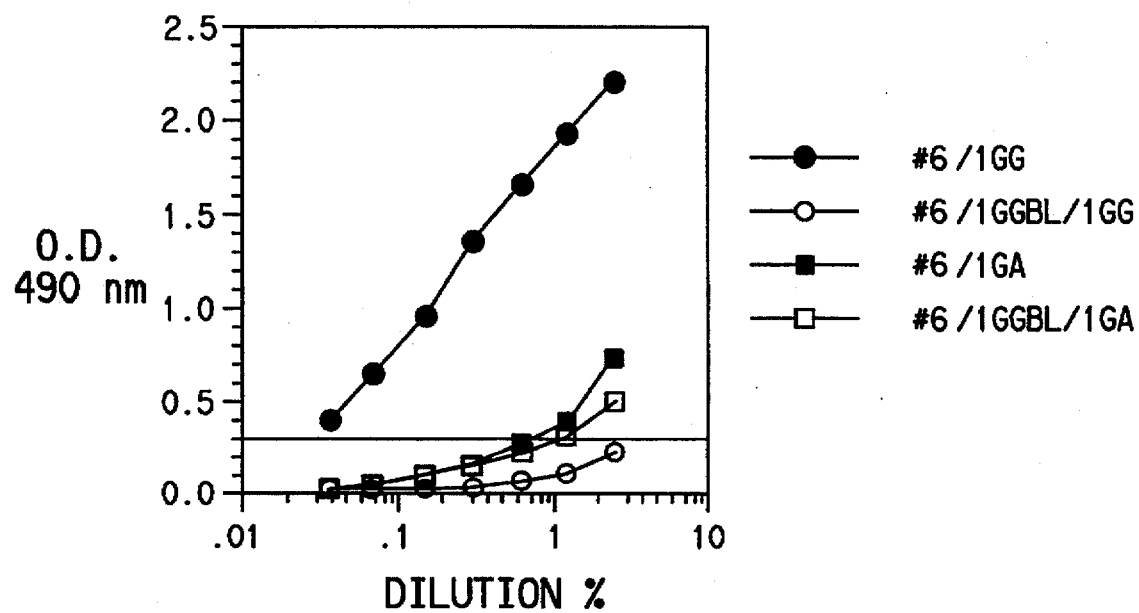
FIG. 7 shows a blocking experiment on samples found to be negative by IFA and found to be low positive having a titer of 1:40 using the assay of this invention.

EBV is coated by a membrane composed of lipid and four major virus-specified proteins, gp350/300, gp220/200, p140, and gp85. The EBV membrane antigen(s) which can be used in the assay of this invention have been variously referred to as gp350/300, gp350/220, gp220/200, gp250/200, gp350/220, gp350, gp340, gp320 or gp220. These terms are used interchangeably herein. Hummel et al. (J. Virology 49:413–417, 1984) have shown that a single DNA fragment codes for the messages which are translated into gp350/300 and gp220/200. In the case of the gp220/200 a portion of the message has been removed by a splicing event. These proteins are important viral antigens for assaying mammalian immunity to viral infection and, in particular, human immunity to viral infection. The assay of this invention can be used to detect and/or quantify a mammalian antibody response to gp350/300. This assay can be used to detect EBV infection or screen an individual suspected of being at risk for developing nasopharyngeal carcinoma. It is believed that a similar assay can also be used to detect a mammalian antibody response to other EBV-MA's such as p140 and gp85. The assay of this invention comprises: (a) incubating a sample suspected to contain EBV/MA antibodies with immobilized EBV-MA; and (b) detecting and/or quantifying the product of step (a) with a detector reagent which is capable of binding mammalian antibodies specific for EBV-MA.

Any immunoglobulin such as IgA, IgG, and/or IgM can be detected or quantified using the assay described herein. In a preferred embodiment, it is a human IgA response which is detected and/or quantified.

Any EBV-MA, be it native antigen, either as whole EBV-infected fixed cells, virus infected cell lysates, or affinity purified antigens from virus infected cell lysates, synthetic antigen, recombinant antigen, or a polypeptide of EBV-MA can be immobilized on the surface of a suitable support using techniques well known to those skilled in the art. The preferred EBV-MA for practicing the invention is a recombinant protein (gp350/220, truncated form) secreted by GH3Δ19 cells which comprise a mammalian cell expression system. The synthesis of this recombinant protein is described in Whang et al., J. Virol., 61(6):1796–1807 (June 1987), the disclosure of which is hereby incorporated by reference.

The support can be any one of a wide variety of supports. There can be mentioned: synthetic polymer supports, such as polystyrene, polypropylene, substituted polystyrene, e.g., aminated or carboxylated polystyrene, polyacrylamides, polyamides, polyvinylchloride, etc.; glass beads, agarose, etc. The supports may include reactive groups to permit direct linking of EBV-MA to the support.

In a preferred embodiment, the support consists of polystyrene microtiter plate wells.

The detector reagent should be capable of binding mammalian antibodies specific for EBV-MA. Preferably, the detector reagent is an anti-antibody labeled with an enzyme, radioactive isotope, fluorogenic, chemiluminescent or electrochemical materials. More preferably, the anti-antibody is an anti-human immunoglobulin class reagent. In addition, the detector reagent should not cross-react with other mammalian immunoglobulin classes.

Enzymes which can be used as labels in the assay of the invention include, but are not limited to, horseradish peroxidase, alkaline phosphatase, beta-galactosidase, glucose oxidase, luciferase, beta-lactamase, urease and lysozyme. Labeling with enzymes is facilitated by using dialdehyde, carbodiimide coupling, homobifunctional crosslinkers and heterobifunctional crosslinkers as described below for labeling antibodies with members of specific binding pairs. The labeling method chosen depends on the functional groups available on the enzyme and the material to be labeled. Any conventional method can be used to label antibodies. This includes the methods described by Engvall and Pearlmann, Immunochemistry 8, 871 (1971), Avrameas and Ternynck, Immunochemistry 8, 1175 (1971), Ishikawa et al., J. Immunoassay 4(3):209–237 (1983) and Jablonski, Anal. Biochem. 148:199 (1985). Labeling can be accomplished by indirect methods such as using spacers or other members of specific binding pairs.

Horseradish peroxidase is the preferred enzyme label.

Antibodies can also be labeled with a member of a specific binding pair which can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, i.e., a hapten, it can be covalently coupled to a carrier protein to render it immunogenic.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin may be covalently coupled to antibodies by utilizing commercially available active derivatives. Some of these are biotin-N-hydroxysuccinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfonate or 2,4-dinitrofluorobenzene. Other standard methods of conjugation may be employed to couple antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent, 1-ethyl-3-(dimethylaminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups may be a photoactive aryl nitrene, which upon irradiation reacts with a variety of groups.

In order to facilitate signal detection, either the antibodies or a member of a specific binding pair can be labeled.

The term antibody as used herein means polyclonal, monoclonal, an immunoreactive fragment thereof, or a mixture of antibodies. The term immunoreactive fragment means a fragment or fragments which contain the binding region of the antibody. Such fragments can be Fab-type fragments which are defined as fragments devoid of the Fc portion, e.g., Fab, Fab', and F(ab')$_2$ fragments, or can be so-called "half-molecule" fragments obtained by reductive cleavage of the disulfide bonds connecting the heavy chain components of the intact antibody.

Antibodies can be prepared using standard techniques well known to those skilled in the art.

This invention provides an alternative method having increased sensitivity, specificity for mammalian antibody responses to EBV-MA, and is more objective than the currently employed EBV-MA IFA.

The following illustrates the practice of the invention.

EXAMPLE 1

A. Production and Purification of Recombinant EBV-MA gp350/220

A transfected rat pituitary cell line, GH3Δ19 (obtained from E. Kieff, Brigham and Women's Hospital, Boston, Mass., the production of which is described in Whang et al., J. Virol., 61(6):1796–1807 (June 1987), the disclosure of which is hereby incorporated by reference as was noted above), or a clone of this line was grown for seven days in 150 cm$^2$ tissue culture flasks or roller bottles maintained in Dulbecco's Modified Eagle's Medium, high glucose, 10% NuSerum (Collaborative Research, Bedford, Mass.) and glutamine at 37° C.

The GH3Δ19 cells secrete high amounts of the recombinant protein gp350/220 (rMA) in a soluble, truncated form which was harvested from the culture supernatants by a two-step purification protocol described below. Periodic cloning and recloning of this cell line, identifying successive high level secretor progeny clones, was necessary to insure high yields of rMA in the recombinant cell supernatants since the amount of secreted protein decreases with increasing passage number. Production of extracellular rMA was monitored by Western blots and ELISA using monoclonal antibodies obtained from hybridoma cell lines, 2L10 and BMA17.3 (obtained from G. Pearson, Georgetown Univ. Medical School, Washington, D.C.).

These monoclonal antibodies were produced using techniques well known to those skilled in the art. Kennett et al.'s protocol modified as described below was used. (Kennett et al., Curr. Top. Microbiol. Immunol. 81:77–91 (1978) as described in Qualtiere et al., Immunology, 79:616–620 (January 1982), the disclosures of which are hereby incorporated by reference.)

Hybridoma cell line 2L10 is directed against gp350/300 of the EBV-MA complex. It was produced according to the procedure described above.

This procedure entails immunizing two mice intraperitoneally with virus-positive cells from the P3HR-1 cell line. The first immunization was in complete Freund's adjuvant while the second immunization was given 3 weeks later in incomplete Freund's adjuvant. The last immunization was given 2 weeks later and consisted of cells alone. Hybridomas were established according to the protocol of Kennett et al., Curr. Top. Microbiol. Immunol., 81:77–91 (1978) as described in Qualtiere et al., supra.

Three days after the last immunization, the spleens were removed. Spleen cells ($10^8$) cells per ml) were mixed with $10^7$ NS-1 myeloma cells and the mixture was pelleted at 900× g for 5 min. The supernatant was discarded and the cells were washed once with S—O medium (RPM1-1640 medium supplemented with 4.5 g of glucose per liter and 10 ml of 200 mM glutamine). All medium was then drained from the tubes and the pellets were gently resuspended in 0.2 ml of 30% polyethylene glycol 1500 (J. T. Baker, Phillipsburg, N.J.). The cells were exposed to polyethylene glycol for 8 min and centrifuged at 900× g for 3 min of this 8 min period, after which 5 ml of S—O medium was added and the cells were recentrifuged at 900× g for 5 min. The pellet was then resuspended in 30 ml of HAT medium (0.1 mM hypoxanthine/0.4 μM thymidine) in S-20 medium (S—O medium plus 20% fetal calf serum and 10% NCTC 135) at a concentration of 1–2×10$^6$ cells per ml. The cells were distributed into each of the wells in 96-well microtiter plates and fed every 3 days with HAT medium. Wells with visible clones were marked and the supernatant fluids from such wells were assayed for antibodies to EBV-induced MAs.

Clones were screened by immunofluorescence on acetone-fixed smears and on live cells from the p3HR-1 and B-95-8 cell lines to establish the membrane specificity of the antibody. Reactivity with native gp350 was established by immunoblotting, immunoprecipitation, and by ELISA against purified gp350 using the ELISA protocol described by Luka et al. J. Immunological Methods, 67:145–156 (1984). The monoclonal antibody did not react with de-glycosylated gp350 establishing that it was directed against the carbohydrate moiety of this glycoprotein.

Hybridoma cell line BMA17.3 is a hybridoma cell line which secretes a monoclonal antibody against the gp350 polypeptide expressed in E. coli, as described by Whang et al. in J. Virol., 61(6): 1796–1807. BMA17.3 was generated by immunizing two mice with the β-galactosidase fusion protein obtained from E. coli containing the EBV open reading frame encoding for part of gp350 (cloned open reading frame encoding for amino acids 38–796 of the protein portion of gp350). The immunization was that described above. The mice were immunized 3 times. The first intraperitoneal (i.p.) injection utilized complete Freund's adjuvant while the second immunization was performed with incomplete Freund's adjuvant 3 weeks later. The third immunization consisted of the antigen by itself and was given 2 weeks after the second injection. The spleens were removed 3 days after the final immunization and fused with the NS-1 mouse myeloma cell line as described above. Clones were screened by ELISA as described above for antibodies reactive with the β-gal fusion protein. Positive lines were then screened by immunofluorescence on acetone-fixed and live cells from the virus-producing P3HR1 and B-95-8 cell lines to establish the membrane specificity of the antibody. Reactivity with native gp350 was established by both immunoblotting and immunoprecipitation.

A two-step purification protocol was used to purify rMA from pooled GH3Δ19 supernatants. The supernatant pool was loaded onto a lectin affinity column (RCA-II, ricin A chain immobilized on agarose beads, E-Y labs, San Mateo, Calif.) at room temperature (RT) followed by a phosphate buffered saline (PBS) wash. The antigen (rMA) was eluted with 0.1M lactose in PBS. Fractions were tested for the presence of rMA by coating onto 96-well polystyrene microtiter plates (NUNC, Denmark) in PBS, blocking of nonspecific sites with assay buffer (1% bovine serum albumin (BSA) in PBS), incubation with BMA17.3 in assay buffer, followed by goat anti-mouse IgG conjugated to horseradish peroxidase (GAM IgG-HRP, TAGO, Burlingame, Calif.) in assay buffer, The enzymatic reaction was developed with 0.2% o-phenylenediamine (OPD) in substrate buffer (0.009M citric acid, 0.03M $K_2HPO_4$ containing 0.15% $H_2O_2$). Fractions containing significant rMA activity were pooled and dialyzed versus 50 mM Tris-HCl, pH 8.0 at 4° C. After dialysis, the pool of fractions was loaded onto a fast protein liquid chromatography (FPLC) mono-Q ion exchange column (Pharmacia, Sweden) equilibrated with Tris-HCl, pH 8.0 at RT. An NaCl gradient (0.0 to 0.5M) was used to elute the antigen which comes off at ~0.2M NaCl. Fractions were analyzed by ELISA as above for rMA content. In addition to the BMA17.3 ELISA, peak fractions were also examined by Western blot using BMA17.3. EBV antibody positive and negative serum controls were then tested on peak fractions by ELISA and Western blot to determine which fractions should comprise the antigen pool.

B. EBV-MA Assay

An indirect ELISA was used to determine serum IgA antibody titers to EBV MA. Purified rMA obtained as described above was coated onto 96-well polystyrene microtiter plates (NUNC) in PBS at a volume of 50 µl/well overnight at 4° C. The antigen content of each preparation varies and therefore the optimal concentration for plate coating was pre-determined by titration of rMA against EBV antibody positive and negative serum controls. The coated plates were washed three times with PBS and nonspecific binding sites are blocked with 200 µl/well of blocking buffer (10% β-lactose, 2% BSA in PBS) for 2 hours at RT. The blocking solution was removed and plates were dried and stored at 4° C. or washed once with PBS for use in the assay.

Serum samples were diluted 1:20 with sample buffer (10% normal goat serum (NGS), 1% BSA, 0.02% sodium azide in PBS) in polypropylene tubes. The 1:20 sample dilutions were then titrated on rMA coated plates in sample buffer at 50 µl/well volumes by 2-fold serial dilutions from 1:20 to 1:1280 and plates incubated at 37° C. for one hour. Plates were then washed six times with wash buffer (0.05% Tween-20, 0.1% chloroacetamide in PBS). To detect serum IgA bound to the rMA coated plate, goat anti-human IgA conjugated to horseradish peroxidase (GAH IgA-HRP, Jackson ImmunoResearch Labs, West Grove, Pa.) was diluted 1:30,000 in conjugate diluent (10% NGS, 1% BSA, 0.05% Tween-20, 0.1% chloroacetamide in PBS), added at 50 µl/well and plates incubated at 37° C. for one hour. Plates were washed six times with wash buffer. The enzymatic reaction was developed with 50 µl/well of OPD in substrate buffer for 10 minutes in the dark at 37° C. and the reaction is stopped with 50 µl/well of 4.0N $H_2SO_4$. Absorbance at 490 nm with 650 nm reference filter was measured by an automated plate reader (Molecular Devices, Menlo Park, Calif.). The antibody titer of each sample was determined by the last dilution giving an absorbance of 0.3 O.D. A negative control serum (healthy volunteer seronegative for EBV VCA by DuPont EBV VCA ELISAs) tested on each plate had an absorbance of <0.04 O.D. at a 1:20 dilution in this assay.

IgA antibody titers were determined for 52 samples (received from G. Pearson) using the assay of this invention. The results were compared to those obtained by IFA (FIG. 1 and Table 1). 14 out of 25 samples found to be negative by IFA were found to be low positives by the assay of this invention—8 of the 14 samples had titers of 1:20 and 6 of the 14 samples had titers of 1:40 due to the increased sensitivity of the rMA ELISA. All of these samples had high levels of IgG antibodies to EBV-MA. To insure there was no cross-reactivity of the anti-human IgA-HRP with IgG antibodies, a series of blocking studies was performed. FIGS. 2 through 7 show the blocking experiments on the negative IFA samples with ELISA titers of 1:40. In all samples the high levels of IgG antibodies were sufficiently blocked with goat anti-human IgG. Titration curves of IgA antibodies were not significantly altered when the IgG was blocked.

Only one out of 27 IgA/IFA positive samples registered negative by the rMA ELISA. This sample had an IgG titer of >2560 by IFA and an IgA titer of 320. It is possible that due to the extremely high level of IgG antibodies, the anti-human IgA reagent used in the IFA cross-reacted with the IgG antibodies. When this sample was tested on VCA ELISA plates (DuPont), a high IgG titer (>1280) was seen, however, no titer was detected by the anti-human IgA reagent described above on the same plates. The GAH IgA-HRP used in the rMA ELISA was titrated and tested extensively to insure that there was insignificant cross-reactivity with other Ig classes, in particular IgG.

These data demonstrate that the IgA specific response as measured by the assay of this invention correlates with IgA specific response as measured by IFA which has been shown to be useful in detecting EBV infection and/or nasopharyngeal carcinoma. Thus, the assay of this invention can also be used to detect EBV infection and/or to screen an individual suspected of being at risk for developing nasopharyngeal carcinoma.

TABLE 1

| Sample | IGA/IFA | IGA/ELISA | Sample | IGA/IFA | IGA/ELISA |
|---|---|---|---|---|---|
| 1 | — | — | 27 | 320 | 640 |
| 2 | — | 40 | 28 | 80 | 40 |
| 3 | 80 | 160 | 29 | 10 | 40 |
| 4 | — | — | 30 | 10 | — |
| 5 | — | — | 31 | 40 | 640 |
| 6 | — | 40 | 32 | 80 | 320 |
| 7 | — | — | 33 | 20 | 640 |
| 8 | — | 20 | 34 | 80 | 320 |
| 9 | — | 40 | 35 | 80 | 320 |
| 10 | — | — | 36 | 80 | 80 |
| 11 | 80 | 20 | 37 | 80 | 160 |
| 12 | — | 20 | 38 | 80 | 80 |
| 13 | — | 20 | 39 | 160 | 160 |
| 14 | — | 40 | 40 | — | — |
| 15 | — | — | 41 | — | 20 |
| 16 | 160 | 80 | 42 | — | 20 |
| 17 | 40 | >1280 | 43 | — | — |
| 18 | 320 | — | 44 | — | 40 |
| 19 | 160 | 160 | 45 | — | — |
| 20 | 80 | 20 | 46 | — | 20 |
| 21 | 80 | 160 | 47 | 40 | 160 |
| 22 | 80 | 320 | 48 | — | — |
| 23 | 640 | >1280 | 49 | 320 | 1280 |
| 24 | 40 | 160 | GP-2 | — | 20 |
| 25 | 40 | 1280 | IgA neg 4/90 | — | 20 |
| 26 | 160 | 40 | IgA pos 4/90 | 160 | 160 |

What is claimed is:

1. An assay for detecting a mammalian IgA antibody response to Epstein-Barr Virus Membrane Antigen EBV-MA which comprises:

(a) incubating a sample suspected to contain EBV-MA antibodies with an immobilized recombinant form of EBV-MA gp350/220 wherein said EBV-MA is truncated gp350/220 secreted by a mammalian cell expression system and further wherein said truncated gp350/220 lacks the transmembrane anchor domain; and (b) detecting the product step (a) by reacting the product of step (a) with a labeled detector reagent which specifically binds mammalian IgA antibodies specific for EBV-MA, thereby detecting said mammalian antibody response to EBV-MA.

2. An assay according to claim 1 wherein the mammalian antibody response is human antibody response.

3. An assay according to claim 1 wherein the detector reagent is a labeled anti-antibody.

4. An assay according to claim 3 wherein the detector reagent is enzyme-labeled.

5. An assay according to claim 4 wherein the enzyme is horseradish peroxidase.

6. An assay according to claim 1 wherein said assay is used to detect EBV infection or screen an individual suspected of being at risk for developing nasopharyngeal carcinoma.

7. An assay for measuring a mammalian IgA antibody response to Epstein-Barr Virus Membrane Antigen EBV-MA which comprises:

(a) incubating a sample suspected to contain EBV-MA antibodies with an immobilized recombinant form of EBV-MA gp350/220 wherein said EBV-MA is truncated gp350/220 secreted by a mammalian cell expression system and further wherein said truncated gp350/220 lacks the transmembrane anchor domain; and (b) reacting the product of step (a) with a labeled detector reagent which specifically binds mammalian IgA antibodies specific for EBV-MA;

(c) assaying for the amount of product formed in step (b); and (d) comparing the amount of said product formed with a standard curve so as to indicate the amount of EBV-MA antibodies present in the sample.

8. An assay according to claim 7 wherein the mammalian antibody response is a human antibody response.

9. An assay according to claim 7 wherein the detector reagent is a labeled anti-antibody.

10. An assay according to claim 9 wherein the detector reagent is enzyme-labeled.

11. An assay according to claim 10 wherein the enzyme is horseradish peroxidase.

12. An assay according to claim 7 wherein the assay is used to detect EBV infection or screen an individual suspected at risk for developing nasopharyngeal carcinoma.

13. An assay for detecting a human IgA antibody response to Epstein-Barr Virus Membrane Antigen EBV-MA which comprises:

(a) incubating a sample suspected to contain EBV-MA antibodies with an immobilized recombinant form of EBV-MA gp350/220 wherein EBV-MA is a truncated gp350/220 secreted by a mammalian cell expression system and further wherein said truncated gp350/220 lacks the transmembrane anchor domain; and (b) detecting the product of step (a) by reacting the product step (a) with a labeled detector reagent which specifically binds human IgA antibodies specific for EBV-MA, thereby detecting said human IgA antibody response to EBV-MA.

14. An assay for measuring a human IgA antibody response to Epstein-Barr Virus Membrane Antigen EBV-MA which comprises:

(a) incubating a sample suspected to contain EBV-MA antibodies with an immobilized recombinant form of EBV-MA gp350/220 wherein said EBV-MA is a truncated gp350/220 secreted by a mammalian cell expression system and further wherein said truncated gp350/220 lacks the transmembrane anchor domain; and (b) reacting the product of step (a) with a labeled detector reagent which specifically binds mammalian IgA antibodies specific for EBV-MA;

(c) assaying for the amount of product formed in step (b); and (d) comparing the amount of said product formed with a standard curve so as to indicate the amount of human IgA EBV-MA antibodies present in the sample.

15. An assay according to claim 13 or 14 wherein the detector reagent is a labeled anti-antibody.

16. An assay according to claim 15 wherein the detector reagent is enzyme-labeled.

17. An assay according to claim 16 wherein the enzyme is horseradish peroxidase.

18. An assay according to claim 13 or 14 wherein said assay is used to detect EBV infection or screen an individual suspected of being at risk for developing nasopharyngeal carcinoma.

* * * * *